US006966910B2

(12) United States Patent
Ritland

(10) Patent No.: US 6,966,910 B2
(45) Date of Patent: Nov. 22, 2005

(54) DYNAMIC FIXATION DEVICE AND METHOD OF USE

(76) Inventor: Stephen Ritland, 1150 N. San Francisco St., Flagstaff, AZ (US) 86001

( * ) Notice: Subject to any disclaimer, the term of this patent is extended or adjusted under 35 U.S.C. 154(b) by 0 days.

(21) Appl. No.: 10/406,895

(22) Filed: Apr. 4, 2003

(65) Prior Publication Data

US 2003/0191470 A1 Oct. 9, 2003

Related U.S. Application Data

(60) Provisional application No. 60/370,708, filed on Apr. 5, 2002.

(51) Int. Cl.$^7$ .............................................. A61B 17/56
(52) U.S. Cl. ...................................................... 606/61
(58) Field of Search ..................................... 606/61, 59

(56) References Cited

U.S. PATENT DOCUMENTS

| 569,839 A | 10/1896 | Roeloffs |
| 3,470,872 A | 10/1969 | Grieshaber |
| 3,875,595 A | 4/1975 | Froning |

(Continued)

FOREIGN PATENT DOCUMENTS

| EP | 0 820 731 A3 | 1/1998 |
| EP | 0820731 B1 | 5/2003 |
| WO | WO 00/18306 | 4/2000 |
| WO | WO 02/02022 A1 | 1/2002 |
| WO | WO 02/02022 | 1/2002 |
| WO | WO 02/07621 | 1/2002 |
| WO | WO 02/060330 | 8/2002 |
| WO | WO 03/026523 | 4/2003 |
| WO | WO 03/026523 A1 | 4/2003 |
| WO | WO 03/073908 | 9/2003 |
| WO | WO 03/073908 A2 | 9/2003 |
| WO | WO 03/094699 | 11/2003 |
| WO | WO 03/094699 A2 | 11/2003 |
| WO | WO 04/075778 | 9/2004 |
| WO | WO 04/089244 | 10/2004 |

OTHER PUBLICATIONS

Caspar; Technique of Microsurgery: Microsurgery of the Lumbar Spine: Principles and Techniques in Spine Surgery: *Aspen Publications*; 1990; 105–122.
Hilton et al.; "Meditronic Sofamor Danek METRX Microdiscectomy Surgical Technique Brochure": 2000.
Kambin; "Arthroscopic Microdiscectomy: Minimal Intervention in Spinal Surgery"; *National Library of Medicine*; 1991; 67–100.
Kambin; "Percutaneous Posterolateral Discectomy"; *Clinical Orthopaedics and Related Research, Section II*; 145–154119.
Savitz; "Same–Day Microsurgical Arthroscopic Latera–Approach Laser–Assisted (SMALL) Fluoroscopic Discectomy"; *Journal of Neurosurgery*; Jun. 1994; 1039–1045.
Schaffer et al.; "Percutaneous Posterolateral Lumbar Discectomy and Decompression with a 6.9 Millimeter Cannula"; *Journal of Bone and Joint Surgery*; 1991; 822–831.
Sofamor Danek Video Systems Brochure.
Wiltse; "New Uses and Refinements of the Paraspinal Approach to the Lumbar Spine"; *Spine*; 13(6):696–706.
U.S. Appl. No. 10/788,172, filed Feb. 25, 2004, Ritland.
U.S. Appl. No. 10/776,094, filed Feb. 10, 2004, Ritland.

*Primary Examiner*—Eduardo C. Robert
(74) *Attorney, Agent, or Firm*—Sheridan Ross P.C.

(57) ABSTRACT

A dynamic fixation device is provided that allows the vertebrae to which it is attached to move in flexion within the normal physiological limits of motion, while also providing structural support that limits the amount of translation motion beyond normal physiological limits. The present invention includes a flexible portion and two ends that are adapted for connection to pedicle screws.

4 Claims, 5 Drawing Sheets

U.S. PATENT DOCUMENTS

| | | | |
|---|---|---|---|
| 4,041,939 A | * 8/1977 | Hall | 606/61 |
| 4,232,660 A | 11/1980 | Coles | |
| 4,440,168 A | 4/1984 | Warren | |
| 4,481,947 A | 11/1984 | Chester | |
| 4,545,374 A | 10/1985 | Jacobson | |
| 4,573,448 A | 3/1986 | Kambin | |
| 4,617,922 A | 10/1986 | Griggs | |
| 4,620,460 A | 11/1986 | Gonzales, Jr. | |
| 4,686,972 A | 8/1987 | Kurland | |
| 4,736,738 A | 4/1988 | Lipovsek | |
| 4,743,260 A | 5/1988 | Burton | |
| 4,747,394 A | 5/1988 | Watanabe | |
| 4,798,111 A | 1/1989 | Cheeseman | |
| 4,803,976 A | 2/1989 | Frigg | |
| 4,817,587 A | 4/1989 | Janese | |
| 4,862,891 A | 9/1989 | Smith | |
| 4,863,423 A | 9/1989 | Wallace | |
| 4,882,958 A | 11/1989 | McNeeley | |
| 5,002,542 A | 3/1991 | Frigg | |
| 5,002,576 A | 3/1991 | Fuhrmann et al. | |
| 5,026,373 A | 6/1991 | Ray et al. | |
| 5,030,220 A | * 7/1991 | Howland | 606/61 |
| 5,035,232 A | 7/1991 | Lutze et al. | |
| 5,048,379 A | 9/1991 | Gramera | |
| 5,052,373 A | 10/1991 | Michelson | |
| 5,055,104 A | 10/1991 | Ray | |
| 5,084,043 A | 1/1992 | Hertzmann | |
| 5,098,435 A | 3/1992 | Stednitz | |
| 5,106,376 A | 4/1992 | Mononen | |
| 5,129,900 A | 7/1992 | Asher et al. | |
| 5,133,720 A | 7/1992 | Greenberg | |
| 5,135,525 A | 8/1992 | Biscoping | |
| 5,148,724 A | 9/1992 | Rexford | |
| 5,158,543 A | 10/1992 | Lazarus | |
| 5,195,541 A | 3/1993 | Obenchain | |
| 5,275,600 A | 1/1994 | Allard et al. | |
| 5,275,611 A | 1/1994 | Behl | |
| 5,279,567 A | 1/1994 | Ciaglia | |
| 5,292,309 A | 3/1994 | Van Tassel | |
| 5,303,694 A | 4/1994 | Mikhail | |
| 5,306,309 A | 4/1994 | Wagner et al. | |
| 5,312,360 A | 5/1994 | Behl | |
| 5,312,405 A | 5/1994 | Korotko et al. | |
| 5,356,413 A | 10/1994 | Martins et al. | |
| 5,363,841 A | 11/1994 | Coker | |
| 5,415,661 A | * 5/1995 | Holmes | 606/69 |
| 5,431,639 A | 7/1995 | Shaw | |
| 5,431,651 A | 7/1995 | Gobla | |
| D361,381 S | 8/1995 | Koros et al. | |
| 5,439,464 A | 8/1995 | Shapiro | |
| 5,466,238 A | 11/1995 | Lin | |
| 5,472,426 A | 12/1995 | Bonati | |
| 5,474,555 A | 12/1995 | Puno et al. | |
| 5,484,440 A | 1/1996 | Allard | |
| 5,489,274 A | 2/1996 | Chu | |
| 5,489,308 A | 2/1996 | Kuslich et al. | |
| 5,512,038 A | 4/1996 | O'Neal et al. | |
| 5,565,502 A | 10/1996 | Glimcher et al. | |
| 5,591,166 A | 1/1997 | Bernhardt et al. | |
| 5,591,235 A | * 1/1997 | Kuslich | 606/61 |
| 5,593,409 A | 1/1997 | Michelson | |
| 5,601,550 A | 2/1997 | Esser | |
| 5,611,778 A | 3/1997 | Brinon | |
| 5,628,740 A | 5/1997 | Mullane | |
| 5,643,263 A | 7/1997 | Simonson | |
| 5,643,264 A | 7/1997 | Sherman et al. | |
| 5,645,599 A | 7/1997 | Samani | |
| 5,683,463 A | 11/1997 | Godefroy et al. | |
| 5,687,739 A | 11/1997 | McPherson | |
| 5,690,632 A | 11/1997 | Schwartz et al. | |
| 5,691,397 A | 11/1997 | Glimcher et al. | |
| 5,702,455 A | 12/1997 | Saggar | |
| 5,716,415 A | 2/1998 | Steffee | |
| 5,725,528 A | 3/1998 | Errico et al. | |
| 5,735,899 A | 4/1998 | Schwartz et al. | |
| 5,743,853 A | 4/1998 | Lauderdale | |
| 5,746,720 A | 5/1998 | Stouder, Jr. | |
| 5,746,741 A | 5/1998 | Kraus et al. | |
| 5,752,957 A | 5/1998 | Ralph et al. | |
| 5,766,221 A | 6/1998 | Benderev et al. | |
| 5,766,253 A | 6/1998 | Brosnahan, III | |
| 5,782,832 A | 7/1998 | Larsen et al. | |
| 5,785,710 A | 7/1998 | Michelson | |
| 5,792,044 A | 8/1998 | Foley | |
| 5,800,435 A | 9/1998 | Errico et al. | |
| D399,955 S | 10/1998 | Koros et al. | |
| 5,816,257 A | 10/1998 | Chin | |
| 5,827,328 A | 10/1998 | Buttermann | |
| 5,836,948 A | 11/1998 | Zucherman et al. | |
| RE36,020 E | 12/1998 | Moore et al. | |
| 5,851,207 A | 12/1998 | Cesarone | |
| 5,860,977 A | 1/1999 | Zucherman et al. | |
| 5,865,847 A | 2/1999 | Kohrs et al. | |
| 5,865,848 A | 2/1999 | Baker | |
| 5,876,404 A | 3/1999 | Zucherman et al. | |
| 5,882,344 A | 3/1999 | Stouder, Jr. | |
| 5,885,285 A | 3/1999 | Simonson | |
| 5,885,299 A | 3/1999 | Winslow et al. | |
| 5,885,300 A | 3/1999 | Tokuhashi et al. | |
| 5,891,147 A | 4/1999 | Moskovitz et al. | |
| 5,895,352 A | 4/1999 | Kleiner | |
| 5,895,390 A | 4/1999 | Moran et al. | |
| 5,897,593 A | 4/1999 | Kohrs et al. | |
| 5,899,901 A | 5/1999 | Middleton | |
| 5,902,231 A | 5/1999 | Foley | |
| 5,906,616 A | 5/1999 | Pavlov et al. | |
| 5,913,818 A | 6/1999 | Co et al. | |
| 5,928,139 A | 7/1999 | Koros | |
| 5,928,233 A | 7/1999 | Apfelbaum et al. | |
| 5,944,658 A | 8/1999 | Koros et al. | |
| 5,954,635 A | 9/1999 | Foley | |
| 5,954,671 A | 9/1999 | O'Neil | |
| 5,961,516 A | 10/1999 | Graf | |
| 5,967,970 A | 10/1999 | Cowan | |
| 5,968,098 A | 10/1999 | Winslow | |
| 5,971,920 A | 10/1999 | Nagel | |
| 5,976,146 A | 11/1999 | Ogawa | |
| 5,984,924 A | 11/1999 | Asher et al. | |
| 5,996,447 A | 12/1999 | Bayouth | |
| 5,997,539 A | 12/1999 | Errico et al. | |
| 6,007,487 A | 12/1999 | Foley et al. | |
| 6,010,520 A | 1/2000 | Pattison | |
| 6,045,579 A | 4/2000 | Hochshuler et al. | |
| 6,048,342 A | 4/2000 | Zucherman et al. | |
| 6,050,997 A | 4/2000 | Mullane | |
| 6,063,088 A | 5/2000 | Winslow | |
| 6,068,630 A | 5/2000 | Zucherman et al. | |
| 6,074,390 A | 6/2000 | Zucherman et al. | |
| 6,074,393 A | 6/2000 | Sitoto | |
| 6,080,155 A | 6/2000 | Michelson | |
| 6,080,193 A | 6/2000 | Hochshuler et al. | |
| 6,081,741 A | 6/2000 | Hollis | |
| 6,083,225 A | 7/2000 | Winslow et al. | |
| 6,090,112 A | 7/2000 | Zucherman et al. | |
| 6,102,948 A | 8/2000 | Brosnahan, III | |
| 6,113,602 A | 9/2000 | Sand | |
| 6,117,137 A | 9/2000 | Halm et al. | |
| 6,117,174 A | 9/2000 | Nolan | |
| 6,120,434 A | 9/2000 | Kimura | |
| 6,120,506 A | 9/2000 | Kohrs et al. | |
| 6,123,705 A | 9/2000 | Michelson | |

| | | |
|---|---|---|
| 6,123,706 A | 9/2000 | Lange |
| 6,132,430 A | 10/2000 | Wagner |
| D433,296 S | 11/2000 | Yamakawa |
| 6,149,652 A | 11/2000 | Zucherman et al. |
| 6,149,686 A | 11/2000 | Kuslich et al. |
| 6,152,871 A | 11/2000 | Foley |
| 6,152,926 A | 11/2000 | Zucherman et al. |
| 6,156,006 A | 12/2000 | Brosens |
| 6,156,038 A | 12/2000 | Zucherman et al. |
| 6,159,179 A | 12/2000 | Simonson |
| 6,162,170 A | 12/2000 | Foley |
| 6,162,236 A | 12/2000 | Osada |
| D436,513 S | 1/2001 | Yamakawa |
| 6,176,823 B1 | 1/2001 | Foley |
| 6,179,838 B1 | 1/2001 | Fiz |
| D438,074 S | 2/2001 | Marr |
| 6,183,471 B1 | 2/2001 | Zucherman et al. |
| 6,190,387 B1 | 2/2001 | Zucherman et al. |
| 6,190,414 B1 | 2/2001 | Young et al. |
| 6,197,002 B1 | 3/2001 | Peterson |
| 6,206,822 B1 | 3/2001 | Foley |
| 6,206,826 B1 | 3/2001 | Mathews et al. |
| 6,206,885 B1 | 3/2001 | Ghahremani et al. |
| 6,206,922 B1 | 3/2001 | Zdeblick et al. |
| 6,206,923 B1 | 3/2001 | Boyd et al. |
| 6,210,413 B1 | 4/2001 | Justis et al. |
| 6,214,004 B1 | 4/2001 | Coker |
| 6,217,509 B1 | 4/2001 | Foley |
| 6,224,597 B1 | 5/2001 | Coker |
| 6,224,608 B1 | 5/2001 | Ciccolella |
| 6,224,631 B1 | 5/2001 | Kohrs |
| 6,235,030 B1 | 5/2001 | Zucherman et al. |
| 6,238,397 B1 | 5/2001 | Zucherman et al. |
| 6,245,072 B1 | 6/2001 | Zdeblick et al. |
| 6,248,106 B1 * | 6/2001 | Ferree .................. 606/61 |
| 6,258,097 B1 | 7/2001 | Cook |
| 6,261,287 B1 | 7/2001 | Metz-Stavenhagen |
| 6,264,658 B1 | 7/2001 | Lee et al. |
| 6,267,763 B1 | 7/2001 | Castro |
| 6,267,764 B1 * | 7/2001 | Elberg .................. 606/61 |
| 6,267,765 B1 | 7/2001 | Taylor et al. |
| 6,270,498 B1 | 8/2001 | Michelson |
| 6,283,966 B1 | 9/2001 | Houfburg |
| 6,287,313 B1 | 9/2001 | Sasso |
| 6,287,343 B1 | 9/2001 | Kuslich et al. |
| 6,290,700 B1 | 9/2001 | Schmotzer |
| 6,293,949 B1 | 9/2001 | Justis et al. |
| 6,296,609 B1 | 10/2001 | Brau |
| 6,312,432 B1 | 11/2001 | Leppelmeier |
| 6,332,883 B1 | 12/2001 | Zucherman et al. |
| 6,342,057 B1 | 1/2002 | Brace |
| 6,348,058 B1 | 2/2002 | Melkent et al. |
| 6,354,176 B1 | 3/2002 | Nordlin |
| 6,368,350 B1 | 4/2002 | Erickson et al. |
| 6,368,351 B1 | 4/2002 | Glenn et al. |
| 6,371,959 B1 | 4/2002 | Trice |
| 6,371,968 B1 | 4/2002 | Kogasaka |
| 6,391,058 B1 | 5/2002 | Kuslich et al. |
| 6,395,033 B1 | 5/2002 | Pepper |
| 6,418,821 B1 | 7/2002 | Yamakawa |
| 6,428,472 B1 | 8/2002 | Haas |
| 6,440,169 B1 | 8/2002 | Elberg et al. |
| 6,443,989 B1 | 9/2002 | Jackson |
| 6,461,330 B1 | 10/2002 | Miyagi |
| D466,766 S | 12/2002 | Marty |
| 6,520,907 B1 | 2/2003 | Foley |
| 6,524,238 B2 | 2/2003 | Velikaris et al. |
| 6,530,926 B1 | 3/2003 | Davison |
| 6,540,756 B1 | 4/2003 | Vaughan |
| 6,551,320 B2 * | 4/2003 | Lieberman .................. 606/61 |
| 6,565,569 B1 | 5/2003 | Assaker et al. |
| 6,692,434 B2 | 2/2004 | Ritland |
| 6,736,816 B2 | 5/2004 | Ritland |
| 2001/0005796 A1 | 6/2001 | Zdeblick et al. |
| 2001/0010021 A1 | 7/2001 | Boyd et al. |
| 2001/0012942 A1 | 8/2001 | Estes |
| 2001/0027320 A1 | 10/2001 | Sasso |
| 2001/0047207 A1 | 11/2001 | Michelson |
| 2002/0011135 A1 | 1/2002 | Hall |
| 2002/0016592 A1 | 2/2002 | Branch |
| 2002/0022764 A1 | 2/2002 | Smith |
| 2002/0029082 A1 | 3/2002 | Muhanna |
| 2002/0049368 A1 | 4/2002 | Ritland |
| 2002/0058948 A1 | 5/2002 | Arlettaz |
| 2002/0068973 A1 | 6/2002 | Jackson |
| 2002/0068975 A1 * | 6/2002 | Teitelbaum et al. ...... 623/17.11 |
| 2002/0077632 A1 | 6/2002 | Tsou |
| 2002/0082695 A1 | 6/2002 | Neumann |
| 2002/0107571 A1 | 8/2002 | Foley |
| 2002/0107572 A1 | 8/2002 | Foley et al. |
| 2002/0120270 A1 * | 8/2002 | Trieu et al. .................. 606/61 |
| 2002/0123668 A1 | 9/2002 | Ritland |
| 2002/0143235 A1 | 10/2002 | Pagliuca |
| 2003/0083688 A1 | 5/2003 | Simonson |
| 2003/0083689 A1 | 5/2003 | Simonson |
| 2003/0093078 A1 | 5/2003 | Ritland |
| 2003/0144665 A1 | 7/2003 | Munting |
| 2003/0171749 A1 * | 9/2003 | Le Couedic et al. .......... 606/61 |
| 2003/0171751 A1 | 9/2003 | Ritland |
| 2003/0187431 A1 | 10/2003 | Simonson |
| 2003/0220689 A1 | 11/2003 | Ritland |
| 2003/0236447 A1 | 12/2003 | Ritland |
| 2004/0002708 A1 | 1/2004 | Ritland |
| 2004/0106997 A1 | 6/2004 | Lieberson |
| 2004/0254428 A1 | 12/2004 | Ritland |
| 2005/0004593 A1 | 1/2005 | Simonson |
| 2005/0020920 A1 | 1/2005 | Ritland |

\* cited by examiner

NEUTRAL POSITION

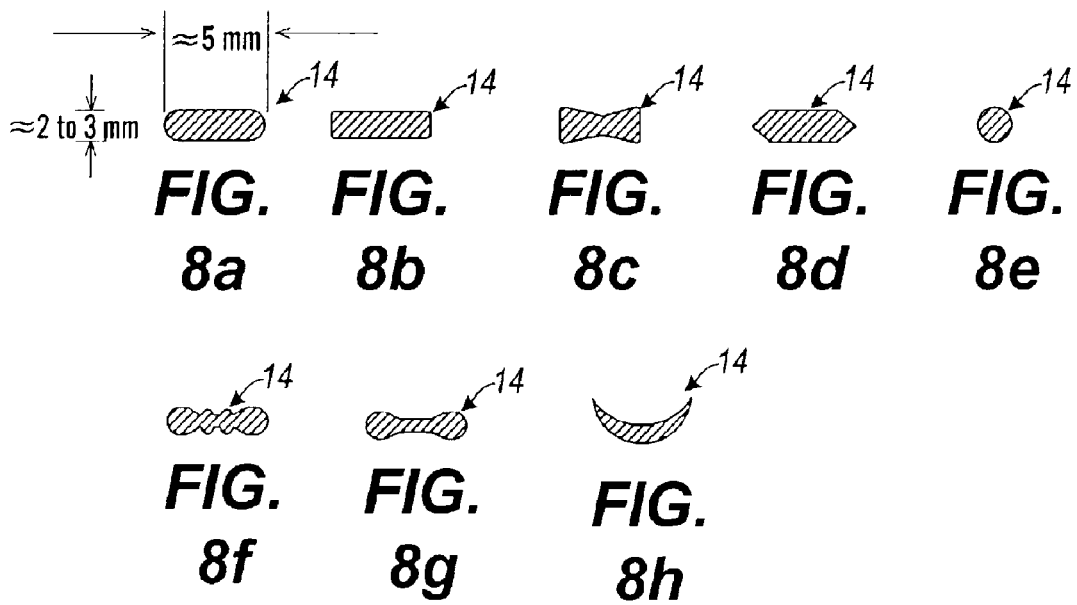
FIG. 8a  FIG. 8b  FIG. 8c  FIG. 8d  FIG. 8e
FIG. 8f  FIG. 8g  FIG. 8h
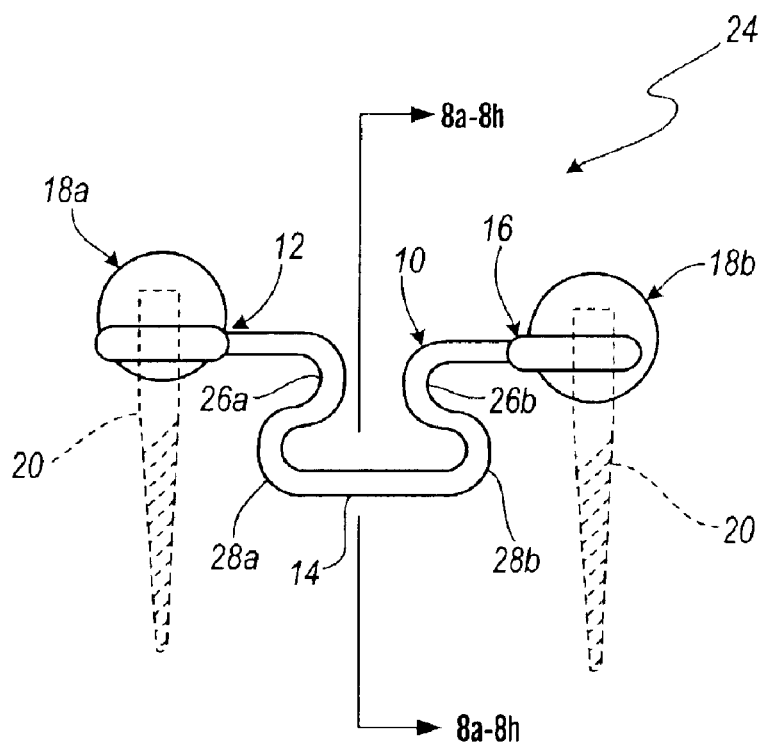
FIG. 9

FIG. 11a  FIG. 11b  FIG. 11c  FIG. 11d

DYNAMIC FIXATION DEVICE AND METHOD OF USE

CROSS-REFERENCE TO RELATED APPLICATIONS

Priority is claimed from U.S. Provisional Patent Application No. 60/370,708 filed Apr. 5, 2002 entitled "Dynamic Fusion System" which is incorporated herein by reference in its entirety.

FIELD OF THE INVENTION

This invention relates generally to securement devices and, more particularly, to a flexible rod or device along a portion thereof that is capable of flexibly securing vertebrae together.

BACKGROUND OF THE INVENTION

The lumbar spine absorbs a remarkable amount of stress and motion during normal activity. For the majority of the population, the healing response of the body is able to stay ahead of the cumulative effects of injury, wear, and aging, and yet still maintain stability with reasonable function. In some cases, however, the trauma or stress exceeds the ability of the body to heal, leading to local breakdown and excessive wear, and frequently also leads to local instability. Accordingly, degenerative change with age superimposed on baseline anatomy in the lumbar spine lead to problems including instability, pain and neurologic compromise in some patients. In some cases, the local anatomy may not provide the same protection to the motion segment, thereby aggravating this breakdown. Although rehabilitation, conditioning, the limitation of stress, and time to recover are effective treatments for most patients, there is a significant failure rate with persistent pain, disability and potential neurologic deficit.

Referring now to FIGS. 1, and 2, two side views of a pair of adjacent vertebral bodies are shown. FIG. 1 illustrates two vertebra $V_1$ and $V_2$ of the spine in a neutral position. As shown in FIG. 2, when a person leans forwards, the spine undergoes flexion. The anterior portion of the spine comprises a set of generally cylindrically shaped bones which are stacked one on top of the other. These portions of the vertebrae are referred to as the vertebral bodies $VB_1$ and $VB_2$, and are each separated from the other by the intervertebral discs D. The pedicles $P_1$ and $P_2$ comprise bone bridges which couple the anterior vertebral body VB to the posterior portion of each vertebra. At each intervertebral joint or disc D, flexion involves a combination of anterior sagittal rotation and a small amplitude anterior translation.

The intervertebral joint is a complex structure comprising an intervertebral disk anteriorly, and paired zygapophyseal joints posteriorly. The disk functions as an elastic support and connection between the vertebra, and allows for flexion and extension of the spine, as well as limited rotation and translation. The zygapophyseal joints and associated anatomy allow for significant flexion and extension while providing constraints in translation and rotation.

The primary bending motion in the lumbar spine is flexion and extension in an anterior/posterior plane. This occurs in the range approximating 10–15 degrees of flexion and extension. In a young or normal lumbar spine, this motion occurs about an axis in the mid to posterior portion of the disk. This is associated with a distraction or subluxation of the facet joints or posterior elements of 10–15 mm. This occurs not about a pure axis, but about a neutral zone, or a centroid of rotation associated with the lumbar disk. The normal elasticity of the disk, joints and ligaments, and the degree of play or freedom associated with these joints, as well as the nature of the loads applied to the spine contribute to the size of this region of rotation. In some cases, the recurrent loads and motion on the disk and associated trauma to disk and motion segment exceed the natural rate of healing or repair of the body. In this situation, there is breakdown in the motion segment associated with loss of the normal axis of rotation. As increasing subluxation occurs with segmental motion, there is a dramatic shift in the axis of rotation with displacement occurring within the disk space or frequently to some point outside of the disk. Therefore, in the situation of a failing motion segment, there is breakdown in the centroid of rotation with associated translation of the vertebral segments. This translation is allowed by both breakdown occurring in the disk and instability associated with both wear and degeneration of the zygapophyseal joints. The underlying anatomy of the motion segment and joints allows for significantly greater stress on the disc and contributes to degeneration both in the disk and joints.

Traditionally, surgical treatment has been directed at treating neural compromise, or if the pain, instability, or risk of instability is considered sufficient, a segmental fusion has been considered. More recently, stabilization procedures have been tried over the past several years including artificial disks and ligaments and elastomeric constructs to protect the spine. Arthroplasty techniques to maximize function and reduce the dynamic effects on adjacent segments are a more recent approach with less follow-up as to long-term results. A challenge in designing such a system is constraining motion in a normal physiologic range.

Current spinal fixation systems offer several drawbacks. Rigid fusion constructs do not allow relative movement between the vertebrae that are fused using a construct comprising a pedicle screw, connector mechanism, and rigid rod. Furthermore, rigid implants are known to create significant amounts of stress on the components of the construct, including the pedicle screws and the rod, as well as the bone structure itself. These stresses may even cause the rigid rod to break. In addition, the stresses transferred to the pedicle screws may cause the screws to loosen or even dislodge from the vertebrae, thereby causing additional bone damage.

Spinal fusion surgery is a method of fusing at least two mobile segments of the spine to knit them together as one unit and eliminate motion between the segments. A dynamic fixation device is a quasi-flexible, semi-rigid fixation construct that allows some measure of motion between the vertebrae attached to the dynamic fixation device. Dynamic fixation of the lumbar spine provides means of protecting lumbar structures and allows for healing without proceeding to a lumbar arthrodesis. The constraints on such a system are in some ways different than for a rigid or near rigid construct, such as that used for fusion.

At the present time, pedicle fixation is an accepted method of fixing to the spine. In the situation of a lumbar fusion, a relatively rigid construct is appropriate to stabilize the spine and allow healing of the bony structures. In the situation of providing protection to the lumbar structures, a flexible system is appropriate to limit but not stop the motion of lumbar elements. The flexible elements in such a system need to accomplish several objectives. The primary objective is to allow physiologic motion of the spine, while protecting against excessive or non-physiologic movement. A secondary consideration is to protect the pedicle fixation from undue stress that could loosen the fixation at its bony interface.

Artificial disks may replace a failing disk and approximate a normal centroid or axis of rotation; however, placement of such a device is technically demanding and replaces the normal disk with a mechanical replacement with uncertain long-term results. The artificial disk will be subject to wear without the healing potential of the body to heal itself.

It is also desirable with some patients to have a spinal implant system that allows the vertebral column to settle naturally under the weight of the human body. Human bone heals more readily under some pressure. In a rigid spinal implant system, the patient's spinal column may be unnaturally held apart by the structure of the implant. It is possible that this stretching of the vertebrae, in relation to one another, results in delayed or incomplete healing of the bone.

Posterior devices placed with pedicle fixation may provide some stabilization, however, the natural motion of such devices does not necessarily act to mimic normal physiology. In a healthy lumbar spine the axis of rotation or neutral area for motion is situated near the inferior posterior third of the lumbar disk. A desirable artificial system would closely approximate physiologic motion. However, to date, posterior systems have failed to address these concerns.

Several existing patents disclose fusion devices having at least some partial ability to flex. For example, U.S. Pat. No. 5,415,661 discloses a device that includes a curvilinear rod. The curvilinear shape is designed to provide a specified amount of flexibility, such that the implant supposedly restores normal biomechanical function to the vertebrae of the spine receiving the implant. However, the '661 patent does not disclose a device having structure other than a curvilinear shape that has a radius of curvature of between 0 to 180 degrees. In addition, the '661 patent does not disclose the concept of providing an anteriorly projected pivot point that models the natural articulation of the subject vertebrae by using a structure that provides a virtual rotation zone substantially identical to the rotation zone provided by the patient's vertebrae. In addition, as seen in FIG. 3 of the '661 patent, the device disclosed in the '661 patent utilizes a body 4 having a central section 10 having an anteriorly oriented position relative to its ends 6a, 6b.

U.S. Pat. No. 6,293,949 also discloses a flexible spinal stabilization device that includes a longitudinal portion that includes a series of shapes that have an accordion appearance. The device disclosed in the '949 patent is intended for use along the cervical vertebrae, and it is intended to be installed along the anterior side of the vertebrae.

U.S. Pat. No. 6,440,169 discloses a device that attaches to the spinous processes of two vertebrae and has a leaf spring that allows the device to compress and then recover spontaneously after the stress has ceased. However, the '169 patent does not address a construct that includes an anteriorly projected pivot point that allows the vertebrae to articulate when the spine undergoes flexion.

In view of the above, there is a long felt but unsolved need for a method and system that avoids the above-mentioned deficiencies of the prior art and that provides an effective system that is relatively simple to employ and requires minimal displacement or removal of bodily tissue.

SUMMARY OF THE INVENTION

The present invention provides a device that can be implanted and that provides for a specified amount of forward bending motion, thereby allowing anterior sagittal rotation between the vertebrae that receive the implant. Reference is hereby made for the incorporation of the conventional descriptive terms of motion and other content presented in *Clinical Anatomy of the Lumbar Spine and Sacrum* by Nikolai Bogduk, third edition, published by Churchill Livingstone, 1999. Although anterior sagittal rotation or flexion between vertebrae is normal, significant anterior sagittal translation or sliding motion between vertebrae is not. Thus, by allowing some amount of rotational motion while protecting against translation, the patient's condition or injury can be protected, thus promoting the healing process, while subsequently providing some ability to rotate one vertebra relative to an adjacent vertebra, thereby allowing for improved spinal motion following surgery and recovery. Accordingly, as described herein, various implants, including a number of rod configurations having flexible portions are presented that provide a device having the ability to elongate and bend. Thus, it is a first aspect of the present invention to provide a device that elongates, and a second aspect of the present invention to provide a device that bends. More particularly, present invention is a dynamic fixation device that includes a flexible rod portion, wherein the flexible rod portion can include one or more of the following: a thin section of rod, a curvilinear rod portion, a geometric shape, and a hinge portion. These dynamic fixation devices are constructed of a material of an appropriate size, geometry, and having mechanical properties such that they bend, thus allowing the vertebrae associated with the implant to rotate relative to one another, similar to the movement of a natural spine.

The normal instantaneous axis of rotation of the lumbar spine occurs typically near the lower posterior third of the disk. Conventional pedicle fixation of the spine typically places the fixation rod or plate at the dorsal aspect of the apophyseal joint or posterior to the joint. Therefore, it is appropriate to consider a construct that effectively shifts this rotation point anteriorly toward the physiologic axis.

A group of geometries exist, which if applied to a posterior device, will constrain the subluxation of the segment and maintain the rotation in or close to the normal zone or axis of rotation. The indication for use is to constrain the stresses and motion within a range which will allow the body's normal healing response to maintain adequate competence in the motion segment to avoid development of instability or neurologic deficit and minimize pain or arthritis. The important features allow for maintenance of physiologic motion without the abnormal subluxation or translation that are associated with a degenerating disk and contribute to further degeneration. Thus, it is a separate aspect of the invention to provide a construct that limits excessive subluxation or translation.

Although the motion is complex related to the range of stresses which may be applied, it is nonetheless possible to provide a device so that while in compression, movement is axial or accompanied by slight dorsal translation, and that while in flexion allows both separation of posterior elements and slight ventral translation allowing rotation about the posterior portion of the disk.

Accordingly, it is an aspect of the present invention to provide a device that allows for some limited motion, thereby decreasing the stresses placed on the various component parts of the implant, as well as the affected vertebrae. It is a further aspect of the present invention to provide a device whose motion is designed to model the bending motion of the spine. Several separate embodiments of the present invention accomplish such tasks.

It is a separate aspect of the present invention to provide a construct that geometrically accommodates the human spinal anatomy, while providing a structural member that provides an anteriorly projected zone of rotation.

In a first embodiment, an implantable elastomeric material may be used, or a surgically implantable alloy can be used that is appropriately shaped and thinned to function as a spring and/or pivot. Appropriate shaping and contouring the flexible rod portion allows the flexible rod portion material to function in its elastic range and avoid stress failure. Additionally, this aspect of the invention allows control of how the motion occurs. More particularly, this feature provides a virtual axis of rotation not necessarily centered at the rod, thereby allowing the implant to more closely approximate the normal physiology of the spine. Thus, in the first embodiment provided herein, thinning and/or flattening a rod will allow simple flexion to occur. As the flattened segment is lengthened, progressively more translation may be allowed.

In a second embodiment presented herein, use of a more complex curve on the flexible rod portion allows both flexion and controlled translation, as well as axial settling in the event of an axial load on the spine. Controlling areas of thinning along the curve allows for controlling how the flexible rod portion bends when loaded. In addition, variable adjustment of thinning along the curve provides the ability to control translation, and thereby fine tuning of the effective axis of rotation. Furthermore, creating a curved rather than flat section allows for modification capability to selectively vary the bending characteristics in flexion versus extension, thus allowing a physician to control segmental shifts.

In yet a separate embodiment, a double center section is used to provide additional control of rotation, or allow for translation without rotation. The double center section includes a arcuate member and an inverted T-shaped member. The members are appropriately thinned or flattened sufficiently to allow controlled bending in flexion. Thus, the dual members may take on a variety of different shapes to achieve the appropriate bending characteristics.

For the above described devices, first and second rod arms are attached to either end of the flexible construct, with the other end of the rod arms attached to connectors, which in turn are connected to pedicle screws that are inserted into vertebrae of the spine. During flexion and extension each vertebra exhibits an arcuate motion in relation to the vertebra below. The center of the arc lies below the moving vertebra. The dynamic fusion device provides a device for allowing movement of the vertebrae, with a forwardly or anteriorly projected pivot location that models and substantially aligns with the actual pivot point of rotation for the vertebrae to which the device is attached. Accordingly, the dynamic fusion device provides a bendable rod for fusion that mimics the movement of the vertebrae of the spine.

The dynamic portions of the various embodiments of the present invention lengthen as they are elongated and shorten as they compressed. This characteristic allows the devices to be implanted in the spine with a pedicle screw system, and while the actual construct is positioned well dorsal in the spine, it will allow the spine to function as though there were a flexible construct in the anterior column of the spine.

In use, a problematic spinal disc is initially identified by a physician. During surgery, an incision is made through the skin and muscle overlying the implant location of the spine. Then a first pedicle screw is inserted into a first vertebra and a second pedicle screw is inserted into a second vertebra. The surgeon then attaches the dynamic fixation device to the pedicle screws using either an adjustable connector or an end connector that is integrally formed as a part of the dynamic fixation device.

Additional advantages of the present invention will become readily apparent from the following discussion, particularly when taken together with the accompanying drawings.

BRIEF DESCRIPTION OF THE DRAWINGS

FIGS. 8a–8h depict cross-sectional views of various potential center sections;

FIG. 9 illustrates a separate embodiment of a dynamic fixation device;

FIGS. 11a–11f depict cross-sectional views of various potential center sections.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

As noted above, at each intervertebral joint or disc D, flexion involves a combination of anterior sagittal rotation and a small amplitude anterior translation. The various embodiments of the present invention allow for controlled rotation while limiting translation within an acceptable, normal physiological range.

Figure 1:
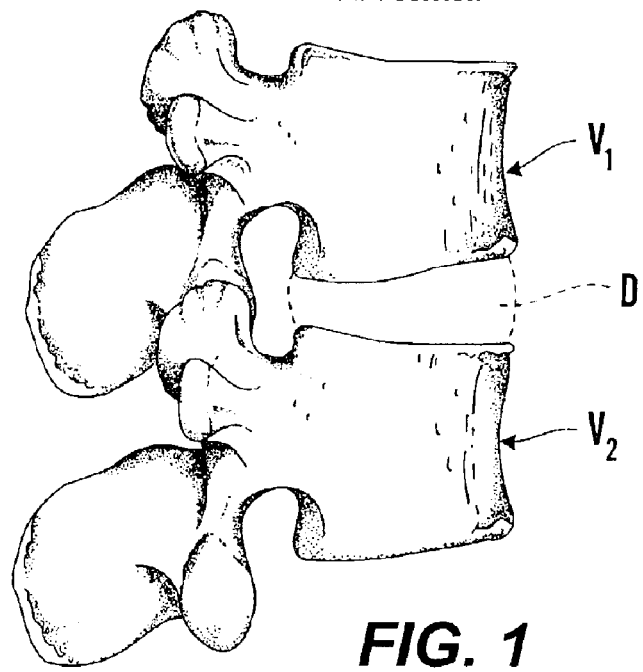
FIG. 1 is a side perspective view of two vertebra in a neutral position.
Figure 2:
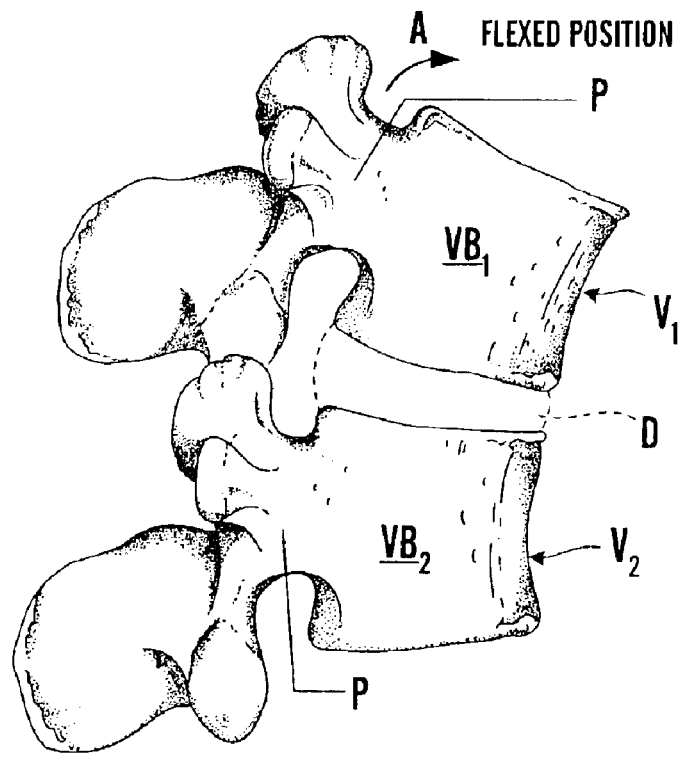
FIG. 2 is a side perspective view of the two vertebra shown in FIG. 1 in a condition of flexion.
Figure 3:
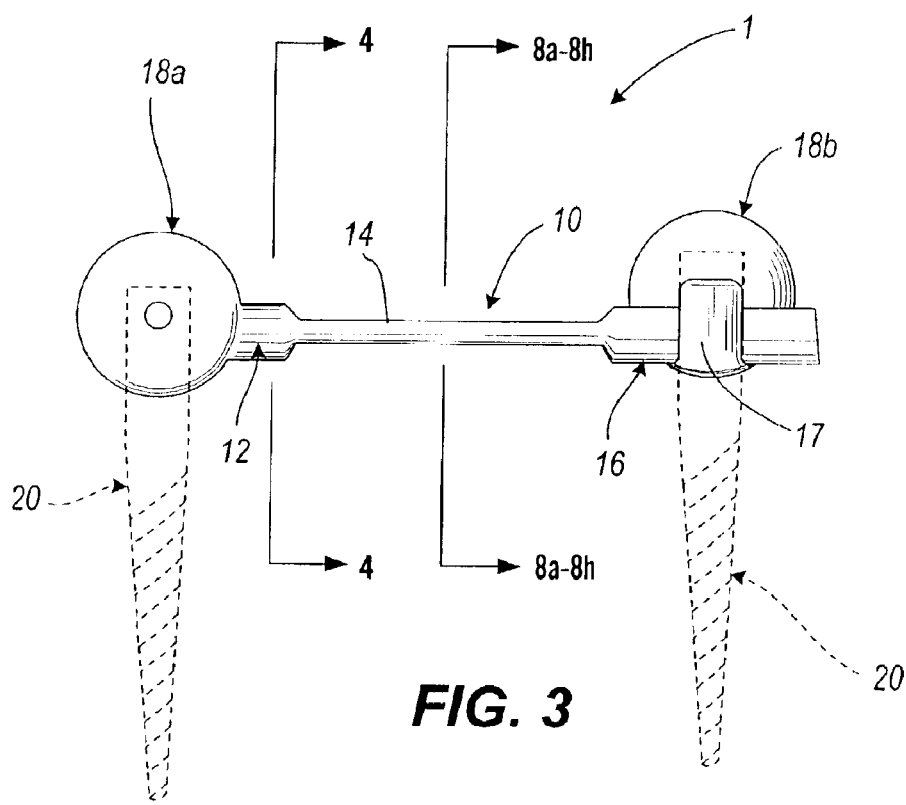
FIG. 3 is a side elevation view of a first embodiment of a dynamic fixation device used in conjunction with pedicle screws.

Referring now to FIG. 3, a first embodiment of a dynamic fixation system 1 is illustrated. The dynamic fixation device 1 includes a rod portion 10 having a first end 12, a center section 14, and a second end 16. First end 12 and second end 16 of rod portion 10 are preferably connected to connectors 18a, 18b that, in turn, are connected to pedicle screws 20, where pedicle screws 20, shown in dashed lines, are inserted into the pedicles of vertebrae when the device is used to fixate vertebrae. In one example of this embodiment, as shown in FIG. 3, rod portion 10 is interconnected at first end 12 to connector 18a. Connector 18a located at first end 12 is of the type that is integrally formed as part of rod portion 10. Alternately, a connector may be a separate type of connector that can be selectively positioned along the length of rod portion 10. For example, connector 18b at second end 16 of rod portion 10 is selectively adjustable and may be interconnected to rod portion 10 at a plurality of positions along second end 16 by slidably adjusting the location of second end 16 within band 17 of connector 18b prior to tightening of connector 18b to interlock the position of second end 16 within connector 18b.

Figure 4:
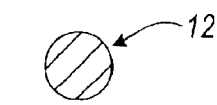
FIG. 4 is a cross-sectional view of a first end of the rod portion of the device shown in FIG. 3.

The center section 14 may have a constant cross-sectional area as shown in FIG. 3. Alternately, as shown in FIG. 3, the cross-section may vary along the length of rod portion 10. FIG. 3 shows the rod portion 10 having a center section 14 with a smaller cross-sectional width than the cross-sectional width of rod portion 10 at first end 12 or second end 16. In one example of this embodiment, rod portion 10 has a circular cross-section at first end 12 and a circular cross-section at second end 16. FIG. 4 depicts one possible cross-section of rod portion 10 at first end 12. As shown in FIG. 3, this is the same cross-section as that located at second end 16, and is typically about 5 mm in diameter.

Figure 5:
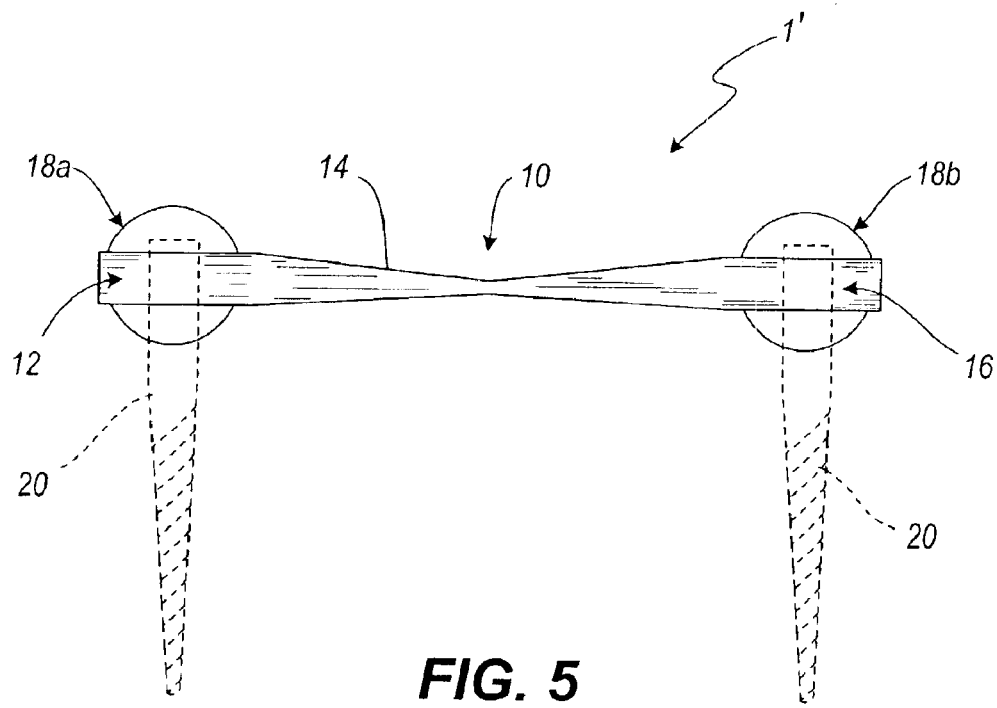
FIG. 5 is a side elevation view of a modified version of the first embodiment shown in FIG. 3.

Referring now to FIG. 5, dynamic fixation device 1' illustrates a modification of the first embodiment wherein the cross-sectional area varies along the length of center section 14 between first end 12 and second end 16. As shown in FIG. 5, a continuously varying cross-sectional area may be used wherein the cross-sectional profile varies continuously along the length of center section 14. More specifically, FIG. 5 depicts one example of this modification to the first embodiment wherein the width of the center section varies from its widest diameter at first end 12 and/or second end 16, and gradually thins to about the center of center section 14.

Figure 6:
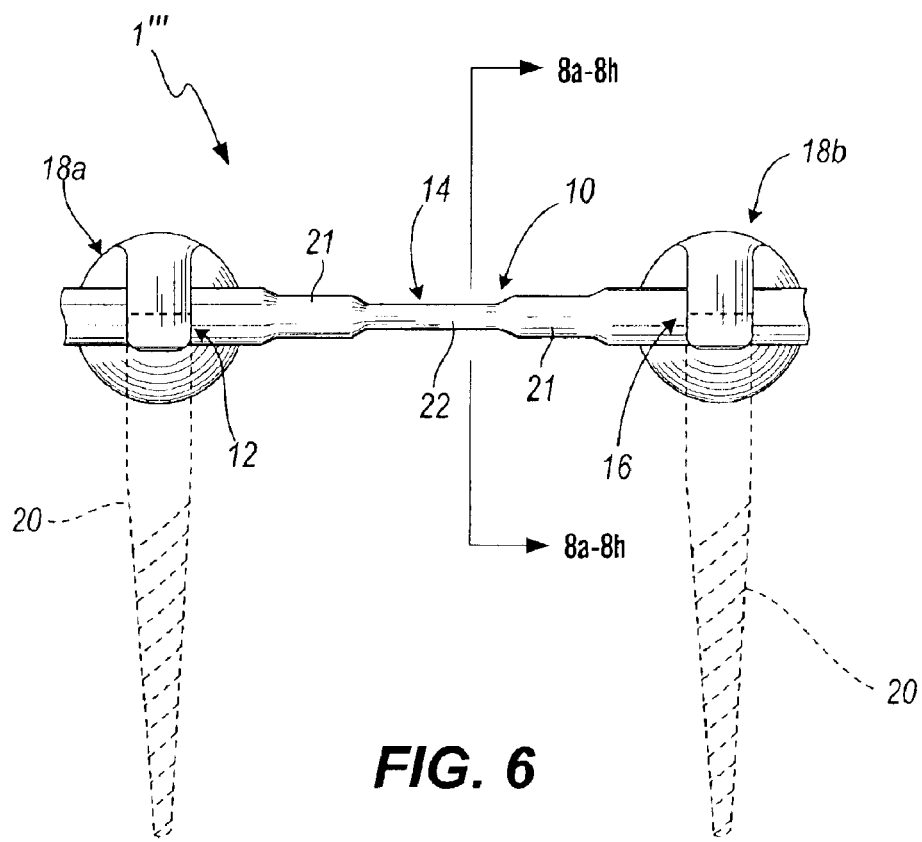
FIG. 6 is a side elevation view of a yet a different modified version of the first embodiment shown in FIG. 3.

Referring now to FIG. 6, the cross-sectional profile of center section 14 may vary at discrete points. FIG. 6 depicts yet a different modification of the first embodiment. Dynamic fixation device 1''' illustrates an example of such a variable profile, wherein a stepwise variable cross-sectional area is provided along center section 14. As shown in FIG. 6, center section 14 can include a first width at first end 12 and second end 16, a second width at intermediate region 21, and a third width at center region 22.

Figure 7:
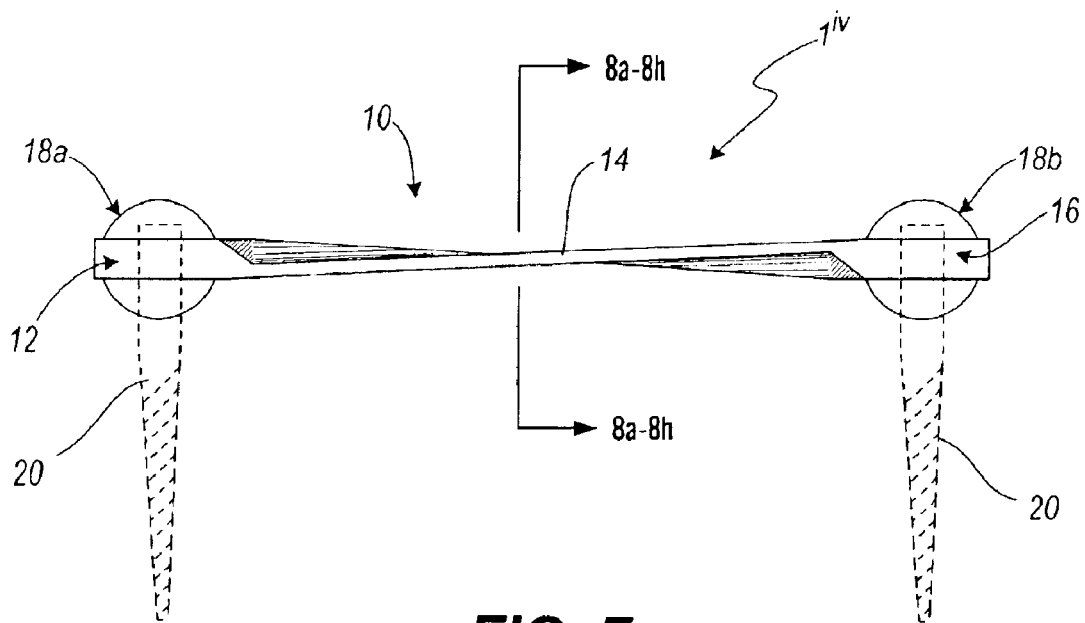
FIG. 7 is a side elevation view of still a yet a different modified version of the first embodiment shown in FIG. 3.

Referring now to FIG. 7, in yet an alternate modification, dynamic fixation device 1$^{IV}$ includes a center section 14 that resembles a twisting ribbon. Center section 14 can be uniform or variable in its width, and is twisted along its length.

The above described alternative configurations offer different bending characteristics, such as the ability to allow a measure of twisting rotation as opposed to only pure bending. Depending upon a patient's circumstances, the attending physician may desire incorporating an implant with one of these different profiles to provide dynamic fixation of the patient's vertebrae.

Referring now to FIGS. 8a–8h, without limitation, the cross-section of center section 14 of rod portion 10 can be of a number of different shapes, and those shapes may vary in cross-sectional area. Preferably, center section 14 has a thickness of about 2 to 3 mm, with a width of about 5 mm. However, the dimensions will vary depending upon the specific design necessary for a specific patient. More particularly, the dimensions of center section 14 will likely be thicker for a large heavy man, as opposed to that needed for a small petite woman. Furthermore, the type of material used to construct center section 14 will also impact the required dimensions of center section 14. Rod portion 10 can be made of a variety of materials, preferably metals or materials demonstrating resilient characteristics, and more preferably, a titanium alloy or surgical stainless steel. In addition, combinations or layers of materials may be used. For example, center section 14 can be formed within its center of material(s) having resilient or rubber like qualities, with a flexible metallic wrapping sufficiently thick to substantially resist translational motion. Such a configuration allows rotational bending and elongation during flexion while preventing the discs from exceeding normal physiologic limits of translational motion. Since different materials have different strength and resilient properties, the type of material used will, in part, dictate the dimensions of the rod portion required to achieve a certain function in a specific patient.

As shown in FIG. 8a, the cross-section of center section 14 of rod portion 10 may be that of an elongated ellipse. Alternately, as shown in FIG. 8b, the cross-section of center section 14 may be that of a flattened rectangle. In yet an alternate variation, the center section 14 may resemble a bow-tie, as shown in FIG. 8c, or a flattened hexagon as shown in FIG. 8d. FIG. 8e depicts a center section 14 having a circular cross-section, but one that is sufficiently small such that is provides the ability to flex or bend. FIGS. 8f–8h depict cross-sections with variable widths, a feature shared with the structure shown in FIG. 8c. FIG. 8h is a crescent shaped center section 14. Therefore, center section 14 can be of a variety of different shapes and yet still provide the necessary flexibility to allow for controlled, limited bending of the spine.

Appropriate shaping and contouring of the center section 14 allows rod portion 10 to function in its elastic range, and avoid stress failure. Furthermore, the center section 14 provides a virtual axis of rotation not necessarily centered at rod portion 10, thereby allowing the implant to more closely approximate the normal physiology of the spine.

Referring now to FIG. 9, a separate embodiment of the dynamic fixation device is illustrated. The dynamic fixation device 24 shown in FIG. 9 includes an inverted T-shaped spring within central region 14. As with the dynamic fixation device 1 shown in FIG. 3, first end 12 and second end 16 of rod portion 10 are interconnected to connectors 18a and 18b, respectively, that are, in turn, connected to pedicle screws 20 that are installed in the pedicles of vertebrae. As with dynamic fixation device 1, the connectors 18a and 18b used with dynamic fixation device 24 may be formed as an integral part of the device 24, or they can be separate, thereby providing adjustability at first end 12 and second end 16. In addition to having a center section 14 that has a relatively thin cross-section that can function in an elastic range yet avoid stress failure as described above, the center section 14 has a shape that is non-linear, as depicted in FIG. 9.

Center section 14 preferably includes at least two bends, and more preferably, a series of bends that add a further spring effect. As noted above, rod portion 10 of the dynamic fixation device 24 depicted in FIG. 9 includes an inverted T-shaped region within center section 14. More particularly, dynamic fixation device 24 includes a first pair of reverse bends 26a and 26b and a second set of reverse bends 28a and 28b. Each reverse bend 26a, 26b, 28a, and 28b in the rod portion 10 is greater than about 90 degrees, and more preferably, each reverse bend is more than about 135 degrees and up to about 180 degrees. That is, rod portion 10 bends at bend 26a at least about 135 degrees and up to about 180 degrees before initiating bend 28a, which also bends at least about 135 degrees and up to about 180 degrees. Reverse bends 26b and 28b are the opposite, but similar in curvature to the bends 26a and 28a, respectively.

The modified dynamic fixation device 24 shown in FIG. 9 helps dampen an axial compression load between the vertebrae interconnected by the device. This construct not only allows for bending between the vertebrae, but also provides a dampening effect for compression loading that occurs between the vertebrae. The inverted T-shaped region of center section 14 shifts the axis of rotation forward, or anteriorly toward the physiologic axis. This allows some axial loading of the spine without unduly stressing the pedicle screw to bone interface.

Similar to dynamic fixation device 1, the center section 14 of dynamic fixation device 24 can have a variety of different cross-sections. The center sections 14 shown in FIGS. 8a–8h present a number of the possible cross-sections that can be used to construct dynamic fixation device 24.

Figure 10:
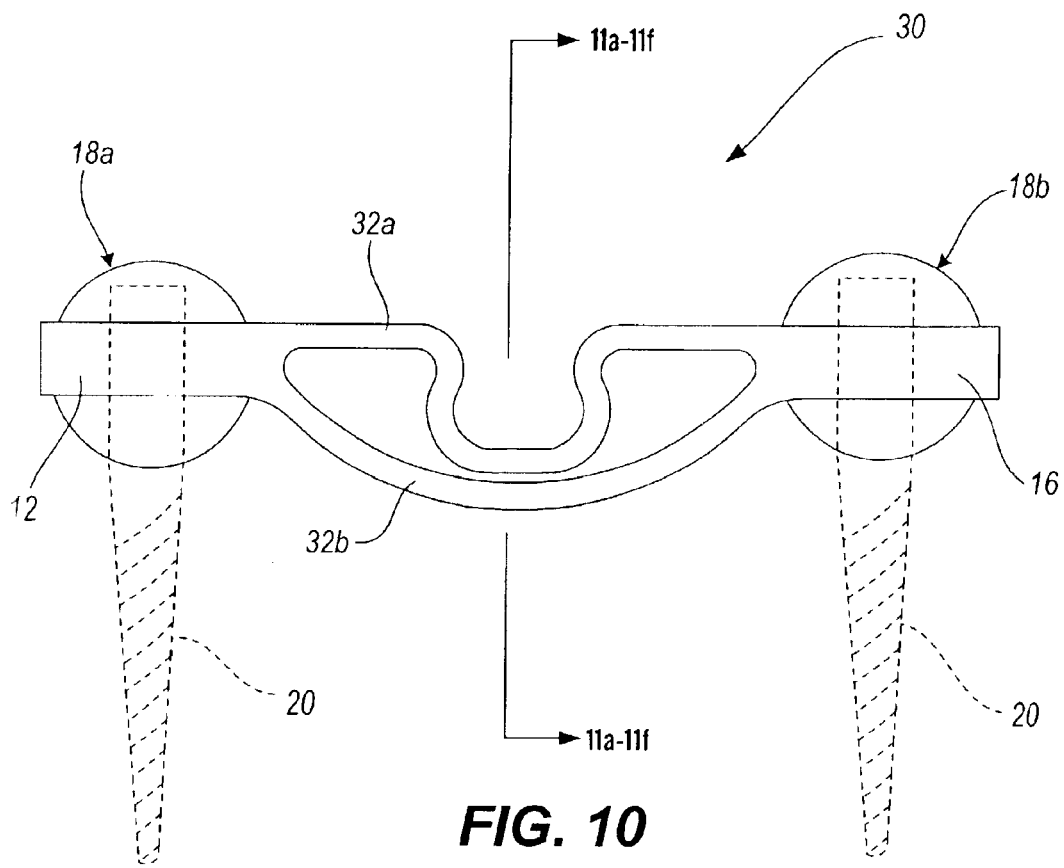
FIG. 10 illustrates a separate embodiment of a dynamic fixation device.

Referring now to FIG. 10, a separate embodiment of a dynamic fixation device 30 is shown. Dynamic fixation device 30 features the ability to provide a device that allows bending, as well as dampening of compression loads, while at the same time providing increased stability. Accordingly, depending upon a patient's attributes, including physical size, age, bone density, and level of activity, the device depicted in FIG. 10 may be more suitable for certain patients.

The functional aspects of the dynamic fixation device 30 are achieved by providing dual central members 32a and 32b. First central member 32a includes an inverted T-shaped region similar to that previously described, and as depicted in FIG. 9. In addition, dynamic fixation device 30 features a second central member 32b that is an arcuate shaped thin section.

The combination of two central members 32a and 32b may be modified in orientation depending upon the patient's needs. More particularly, the arcuate shaped member may be positioned above (not shown) the inverted T-shaped member or adjacent (not shown) the T-shaped member, and not necessarily under the T-shaped member as depicted in FIG. 10. Different orientations provide different characteristics in bending and in compression, as well as in torsion. Thus, various configurations of multiple member dynamic fixation devices are appropriate for addressing specific patient's needs, as the cases may dictate. Furthermore, two T-shaped members in various orientations may be used in contrast to one acuate member and one inverted T-shaped member. Likewise, two acuate members may also be used in combination, to include arcuate members stacked like spoons, arcuate members oriented 180 degrees to each other, or arcuate members disposed 90 degrees to each other.

Figure 11E:
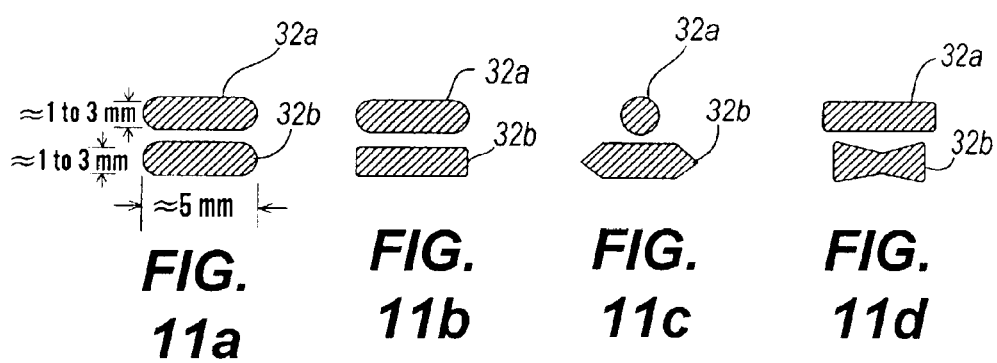
Figure 11E:
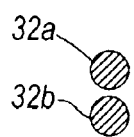
Figure 11F:
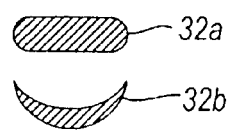

For the embodiment depicted in FIG. 10, various cross-sections for each central member 32a and 32b are possible. Several, but not all possible cross-sectional views are depicted in FIGS. 11a–11f. Two elongated elliptical members are depicted in FIG. 11a. Alternately, central members 32a, 32b may take the form of one elongated elliptical member and one flattened rectangle, as depicted in FIG. 11b. In yet an alternate combination, a relatively small circular member may be used in combination with a flattened hexagonal member, as depicted in FIG. 11c. Alternately, a flattened rectangular member may be used in combination with a bow tie-shaped member, as depicted in FIG. 11d. Other combinations of shapes for central members 32a and 32b not listed here are within the scope of the invention.

In yet a separate embodiment, a dynamic fixation device can utilize a coil portion (not shown) for providing a mechanism for allowing the rod to bend. In an alternate design of this embodiment, a composite material is used to serve as a bendable portion. Whether a coil or composite material is used to form a bendable portion, this embodiment preferably utilizes a mechanism for preventing reverse bending, or posterior sagittal rotation. For example, a separate stiffener may be provided on the posterior side of the coil portion, thereby allowing the device to bend in a forward direction, allowing anterior sagittal rotation, but substantially limiting or preventing bending in a reverse direction, thereby preventing posterior sagittal rotation. Furthermore, multiple stiffeners may be used to limit lateral rotation. That is, additional stiffeners may be incorporated that substantially limit or prevent left or right coronal rotation.

The nature of the coil may be a single winding, a double winding, or it may contain a plurality of windings. In one preferred embodiment, a helix-shaped coil is provided. Coils uncoil when stressed. Composites have physical properties that mimic coiling and uncoiling depending upon the loading conditions. Coils may be used in combination with composite materials, and in combination with stiffeners of various orientations.

In a typical use to span two vertebra, the total length of the dynamic fixation devices 1, 24, and 30 may be approximately 25 to 30 mm. For a dynamic fixation device spanning one joint, it will expand up to approximately 5 to 10 mm in length, and will rotate forward up to between 5 to 10 degrees to accommodate flexion of the spine. Obviously, different size dynamic fixation devices may be used to accommodate the specific needs of each individual patient. More particularly, a relatively large dynamic fixation device may be needed for a large man, while a relatively small dynamic fixation device may be needed for a smaller patient, such as child or a petite woman. However, a limited number of sizes may provide adequate coverage for the majority of the patient population. For any given device, a potential elongation of the dynamic fixation device of approximately 20% is anticipated.

The dynamic fixation devices can be used to flexibly fuse a plurality of vertebra. Alternatively, the dynamic fixation devices can be located at specific points where bending of the spine is desired, while a rigid rod may be used at other locations desired by the physician.

The structures of the present invention are made from one or more materials that possesses the appropriate strength characteristics necessary to withstand loading from the human body when used in medical applications. In addition, the materials are compatible with the human body. Preferably, materials include ceramics, plastics, metals, or carbon fiber composites. More preferably, the materials are made from titanium, a titanium alloy, or stainless steel.

Devices disclosed herein can also be made of thermal memory materials or materials that possess different elastic properties at varying temperatures. In this aspect of the invention, the subject component(s) may be heated or cooled to a desired temperature, implanted, then subsequently allowed to cool or warm to the temperature of the ambient conditions that will exist during the usage period for the subject device, namely, normal body temperature.

It is to be understood that the present invention has application to medical devices other than spinal implants. Furthermore, it is understood that the present invention has application outside the medical field. The dynamic fixation device of the present invention is not limited to medical implants. The device could be used in seismic dampening applications. Alternatively, the present invention could be used to secure any two objects, such as in linking mechanisms, and has application to any type of mechanical device with a moving connection. Other applications, by no means exhaustive, may include connecting any articulated device, such as an implement connection to a tractor. It may also be used in heretofore static type connection applications, such as attaching an antenna to a base structure. One of skill in various of the construction arts will appreciate how to make and use the present invention in view of the guidance provided herein (with respect to a surgical application) and in view of the figures set forth herein.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. In subcombination, an intervertebral bridge linkage device for flexibly fixating a first vertebra of a patient's spine to a second vertebra of the patient's spine, the linkage used in combination with a first connector mechanism and a first pedicle screw for interconnecting the linkage to the first vertebra, and a second connector mechanism and a second pedicle screw for interconnecting the linkage to the second vertebra, the linkage device comprising:

a rod portion including a first end having a first cross-sectional area, a second end having a second cross-section area, and a section disposed between said first end and said second end, wherein said section further comprises an inverted T-shaped region comprising a first pair of reverse bends and a second pair of reverse bends, said section having a smaller cross-sectional area than at least one of either said first cross-sectional area or said second cross-sectional area;

wherein said section flexes when the patient bends their spine.

2. The subcombination as claimed in claim 1, wherein said first pair of reverse bends is at an angle of greater than about 135 degrees.

3. The subcombination as claimed in claim 2, wherein said second pair of reverse bends is at an angle of greater than about 135 degrees.

4. The subcombination as claimed in claim 1, wherein said rod portion comprises a metal alloy.

* * * * *